United States Patent [19]

Kuo et al.

[11] 3,939,182

[45] Feb. 17, 1976

[54] PROSTAGLANDIN E$_1$ INTERMEDIATE 6α-CARBOXY-5α(1-HYDROXYETHYL)-2-CYCLOHEXENE-1-HEPTANOIC ACID,γ-LACTONE, AND LOWER ALKYL OR ARALKYL ESTERS THEREOF

[75] Inventors: Chan-Hwa Kuo, South Plainfield; David Taub, Metuchen; Norman L. Wendler, Summit, all of N.J.

[73] Assignee: Merck & Co., Inc., Rahway, N.J.

[22] Filed: Feb. 11, 1975

[21] Appl. No.: 549,123

Related U.S. Application Data

[62] Division of Ser. No. 406,752, Oct. 15, 1973, which is a division of Ser. No. 290,590, Sept. 20, 1972, Pat. No. 3,850,952.

[52] U.S. Cl............................................ 260/343.3 R

[51] Int. Cl.$^2$........................................ C07D 493/00
[58] Field of Search................................. 260/343.3

[56] References Cited
OTHER PUBLICATIONS

Karrer Organic Chem., (1938), p. 55.

*Primary Examiner*—James A. Patten
*Attorney, Agent, or Firm*—Thomas E. Arther; Harry E. Westlake, Jr.

[57] ABSTRACT

6 α-Carboxy-5α (1-hydroxyethyl)-2-cyclohexene-1-heptanoic acid, γ - lactone, and lower alkyl and aralkyl esters thereof, are useful intermediates for the production of Prostaglandin E$_1$.

2 Claims, No Drawings

PROSTAGLANDIN E₁ INTERMEDIATE 6α-CARBOXY-5α(1-HDROXYETHYL)-2-CYCLOHEXENE-1-HEPTANOIC ACID γ-LACTONE, AND LOWER ALKYL OR ARALKYL ESTERS THEREOF

BRIEF SUMMARY OF THE INVENTION

This is a division of U.S. application Ser. No. 406,752 filed Oct. 15, 1973; which in turn is a division of U.S. application Ser. No. 290,590 filed Sept. 20, 1972, now U.S. Pat. No. 3,850,952 patented Nov. 26, 1974.

This invention relates to a new and novel synthesis of Prostaglandin $E_1$ and more particularly to a synthesis which has a high degree of stereoselectivity at the points of generating the asymmetric centers of the molecule. It relates further to a synthesis in which the yields are high in the several reaction steps. The invention relates still further to the novel compounds obtained as intermediates in the Prostaglandin $E_1$ synthesis and the process of making such intermediates.

DETAILED DESCRIPTION OF THE INVENTION

Prostaglandin $E_1$, which may be depicted structurally as is one of a group of naturally occurring compounds known generally as prostaglandins. These prostaglandins have interesting and important biological activity, the precise biological properties varying with the individual members of the prostaglandin family, as described in the article Prostaglandins, by P. W. Ramwell et al., Progress in the Chemistry of Fats and Other Lipids, Vol. IX, Polyunsaturated Acids, Part 2, pp. 231–273, Pergamon Press (1968).

One of the more important prostaglandins is prostaglandin $E_1$, also known as $PGE_1$. It has an effect on the contractility of smooth muscle and is useful in the induction of labor in pregnant females and for the termination of pregnancies by therapeutic abortion, M. P. Embrey, British Medical Journal, 1970, 2, 256–258; 258–260. Other uses, besides stimulation of smooth muscle, are described in the literature and include the lowering of blood pressure, effect on the mobilization of free fatty acids from adipose tissue, inhibition of lipolysis, and bronchodilating effects.

Heretofore, the supply of prostaglandin $E_1$, as well as of other prostaglandins, has been severely limited because only minute amounts of naturally occurring material are available, and partial biosynthesis by enzymes present in mammalian seminal vesicles has only afforded limited amounts of the products.

An object of this invention is to provide a facile and economic synthesis of racemic prostaglandin $E_1$ which compound has one-half the biological activity of the naturally occurring $PGE_1$.

A further object of the invention is to provide novel intermediate compounds some of which in addition to being useful in the synthesis of racemic (±) $PGE_1$, may themselves exhibit prostaglandin-like activity. An additional object is to provide a stereoselective total synthesis of the other members of the prostaglandin group which may be prepared by known methods from (±) prostaglandin $E_1$. Thus, for instance, (±) prostaglandin $F_{1\alpha}$ may be obtained by reduction of (±) $PGE_1$. Other objects will become evident from the following description of the invention. The novel process and intermediates of our invention are shown structurally in the following flow diagram, and immediately following this diagram the chemical names of the compounds are set forth.

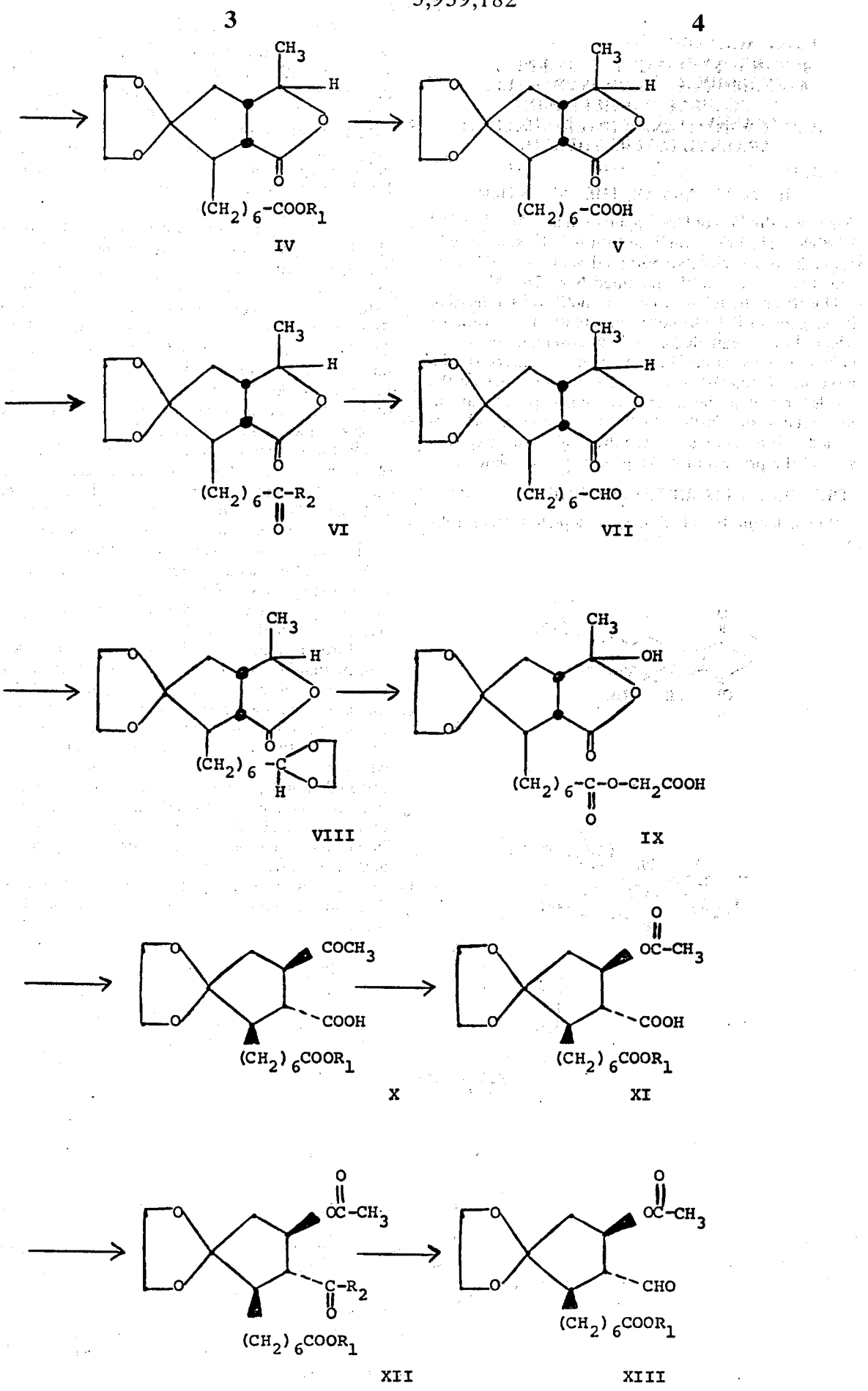

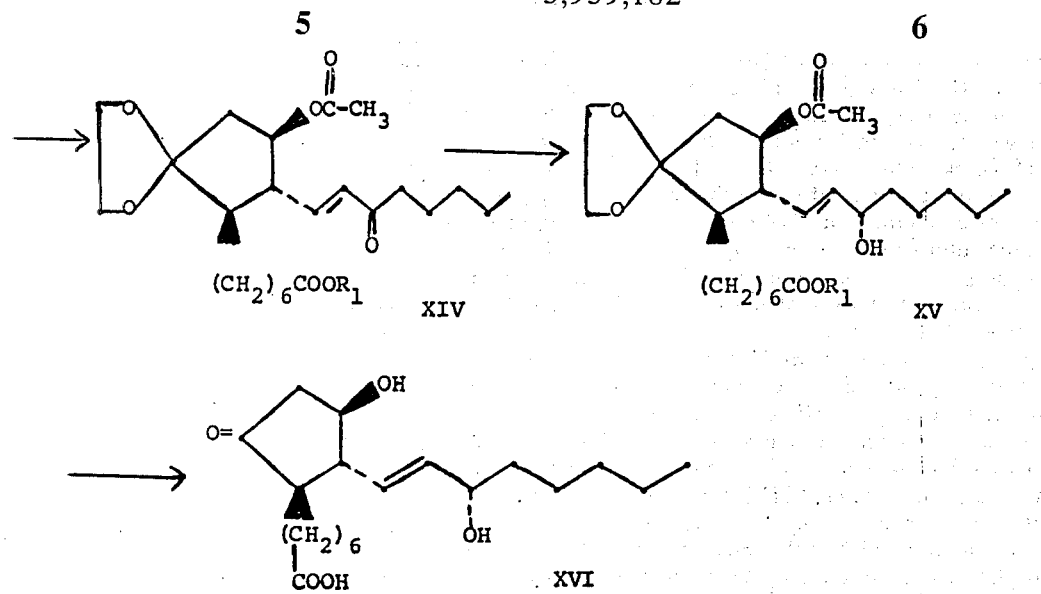

In the foregoing formulae $R_1$ is loweralkyl or aralkyl; and $R_2$ is a halogen, 1-imidazolyl, carbazolyl, aziridinyl, or 3,5-dimethylpyrazolyl. The loweralkyl groups of this invention are those containing from 1 to 6 carbon atoms such as methyl, ethyl, propyl, and hexyl. The aralkyl groups are defined as loweralkyl groups substituted with an aromatic group of from 6 to 10 carbon atoms. Preferred are benzyl, xylyl and the like. The term "halogen" includes the atoms fluorine, chlorine, bromine, and iodine.

As a matter of convenience for understanding the foregoing flowsheet and the following description of the invention, there follows a list of names of the chemical compounds A, B, and I–XVI inclusive.

A - $R_1$ - 8, 10 - undecadienoate
B - β - angelicalactone
I - 6α-Carboxy-5α(1-hydroxyethyl)-2-cyclohexene-1-heptanoic acid loweralkyl or aralkyl ester, γ-lactone.
II - 3-Carboxymethyl-4-methyl-2-[1-carboxy-7-(loweralkoxy or aralkoxy carbonyl)heptyl]-4-hydroxybutyric acid γ-lactone.
III - 2α-Carboxy-3α-(1-hydroxyethyl)-5-oxocyclopentaneheptanoic acid loweralkyl or aralkyl ester, γ-lactone.
IV - 2α-Carboxy-3α-(1-hydroxyethyl)-5-oxocyclopentaneheptanoic acid loweralkyl or aralkyl ester, γ-lactone 5-cyclic ethylene acetal.
V - 2α-Carboxy-3α-(1-hydroxyethyl)-5-oxocyclopentaneheptanoic acid 5-cyclic ethylene acetal, γ-lactone.
VI - 2α-Carboxy-3α-(1-hydroxyethyl)-1-(6-$R_2$-carbonylhexyl)-5-cyclopentanone, 5-cyclic ethylene acetal, γ-lactone.
VII - 2α-Carboxy-3α-(1-hydroxyethyl)-1-(6-formylhexyl)-5-cyclopentanone, 5-cyclic ethylene acetal, γ-lactone.
VIII - 2α-Carboxy-3α-(1-hydroxyethyl)-1-[6-(1,3-dioxolan-2-yl)hexyl]-5-cyclopentanone 5-cyclic ethylene acetal, γ-lactone.
IX - 2α-Carboxy-3α-(1,1,dihydroxyethyl)-5-oxocyclopentaneheptanoic acid, carboxymethyl ester, γ-lactone 5-cyclic ethylene acetal.
X - 3β-Acetyl-2α-carboxy-5-oxo-1β-cyclopentaneheptanoic acid, loweralkyl or aralkyl ester 5-cyclic ethylene acetal.
XI - 3β-Acetoxy-2α-carboxy-5-oxo-1β-cyclopentaneheptanoic acid, loweralkyl or aralkyl ester 5-cyclic ethylene acetal.
XII - 3β-Acetoxy-2α-$R_2$-carbonyl-5-oxo-1β-cyclopentaneheptanoic acid loweralkyl or aralkyl ester 5-cyclic ethylene acetal.
XIII - 3β-Acetoxy-2α-formyl-5-oxo-1β-cyclopentaneheptanoic acid loweralkyl or aralkyl ester 5-cyclic ethylene acetal.
XIV - 3β-Acetoxy-5-oxo-2α-(3-oxo-1-octenyl)-1β-cyclopentaneheptanoic acid, loweralkyl or aralkyl ester 5-cyclic ethylene acetal.
XV - 3β-Acetoxy-5-oxo-2α-(3-hydroxy-1-octenyl)-1β-cyclopentaneheptanoic acid, loweralkyl or aralkyl ester 5-cyclic ethylene acetal.
XVI - Prostaglandin $E_1$.

The synthesis of (±) prostaglandin $E_1$ starts with the condensation of $R_1$ - 8, 10 - undecadienoate (A) and β-angelicalactone (B) in a Diels-Alder reaction. The reaction is generally run in a closed reaction vessel with the preferred temperature in the 150°–250°C. range. A solvent is optional as the reaction is readily performed without one, however, if one is employed a non-reactive aprotic solvent is preferred. In general, however, the only need for a solvent is to facilitate the transfer of the reactants into the reaction vessel. The reaction is generally complete in from 5 to 50 hours in the above temperature range. Preferably the reaction is run at from 20 to 30 hours at 175°–225°C. The substrates react in equimolar quantities but it is preferred, in order to improve the yield based on $R_1$ - 8, 10 - undecadienoate, to maintain an excess of β-angelicalactone over the $R_1$ - 8, 10 - undecadienoate. Generally up to a five molar excess of the lactone is sufficient. The excess lactone is recovered from the reaction mixture and is reusable.

The Diels-Alder adduct, 6α-carboxy-5α(1-hydroxyethyl)-2-cyclohexene-1-heptanoic acid loweralkyl or aralkyl ester γ-lactone (I) is treated with an oxidizing agent capable of selectively cleaving an olefinic bond in order to oxidatively cleave the cyclohexene double bond and form the dicarboxylic acid, viz 3-carboxymethyl-4-methyl-2-[1-carboxy-7-(loweralkoxy or aralkoxy carbonyl)heptyl]-4-hydroxybutyric acid γ-lactone (II). The oxidizing agents of choice are ozone, potassium permanganate, sodium periodate-potassium permanganate and the like. Ozonolysis is the preferred procedure. Owing to the reactivity of ozone the reaction is run at a depressed temperature of from −20° to −80°C. The ozonide intermediate is decomposed by treatment with hydrogen peroxide in acetic acid at from 25°–75°C. The product (II) is isolated by techniques known to those skilled in this art.

The oxidation product, 3-carboxymethyl-4-methyl-2-[1-carboxy-7-(loweralkoxy or aralkoxy carbonyl)heptyl]-4-hydroxybutyric acid γ-lactone (II) is decarboxylated and ring closed affording 2α-carboxy-3α-(1-hydroxyethyl)-5-oxocyclopentaneheptanoic acid loweralkyl or aralkyl ester, γ-lactone (III). The dicarboxylic acid is treated with an acid anhydride such as acetic anhydride and a base which is the alkali metal salt of the carboxylic acid corresponding to the acid anhydride such as sodium acetate. When acetic anhydride is the reactant along with the ketone (III) is formed the enol acetate derivative thereof:

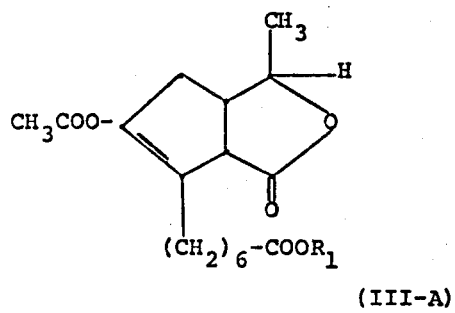

(III-A)

The enol acetate may be hydrolyzed to the desired ketone (III) by acid catalyzed hydrolysis with, for example, hydrochloric acid in a loweralkanol. This will afford pure ketone (III). However, the mixture of (III) and (III-A) may be reacted together in the preparation of the cyclic ethylene acetal derivative, 2α-carboxy-3α-(1-hydroxyethyl)-5-oxocyclopentaneheptanoic acid loweralkyl or aralkyl ester, 5-cyclic ethylene acetal, γ-lactone (IV) by treatment with ethylene glycol and preferably also with an acid catalyst such as p-toluenesulfonic acid monohydrate. Both the ketone group of (III) and the enol acetate of (III-A) are simultaneously converted to the cyclic ethylene acetal function. The reaction is preferably run in a solvent which is not miscible with water such as benzene or toluene which forms an azeotrope therewith which is separable therefrom in a suitable apparatus. In this way the progress of the reaction may be followed by observing the molar quantities of water produced during the reaction. When the calculated amount of water is removed, the reaction is complete. The cyclic acetal is isolated by procedures known to one skilled in this art.

The carboxylic ester function of 2α-carboxy-3α-(1-hydroxyethyl)-5-oxocyclopentaneheptanoic acid loweralkyl or aralkyl ester 5-cyclic ethylene acetal, γ-lactone (IV) is hydrolyzed to the carboxylic acid by base catalyzed hydrolysis in a solvent such as an alkali metal hydroxide in a lower-alkanol. Acid catalyzed hydrolysis cannot be employed in as much as this will cause the hydrolysis of the cyclic acetal also. The reaction is run generally at room temperature although slight cooling or heating will not adversely affect the reaction. A temperature range of 15°–35°C. is permitted with the reaction being complete in from 15 minutes to 3 hours. 2α-Carboxy-3α-(1-hydroxyethyl)-5-oxocyclopentaneheptanoic acid ethylene acetal, γ-lactone (V) is isolated by the usual techniques.

The next step in the synthesis is the reduction of the carboxylic acid group to the aldehyde group. This is accomplished by first replacing the hydroxyl function of the carboxylic acid group of 2α-carboxy-3α-(1-hydroxyethyl)-5-oxocyclopentaneheptanoic acid 5-cyclicethylene acetal, γ-lactone (V) with a suitable leaving group such as an imidazole, carbazole, aziridine, or 3,5-dimethyl pyrazole groups, a halide or the like. It is preferred to form the imidazolyl and the like derivatives with reagents as N,N'-carbonyldiimidazole. The reaction is run in a non-hydroxylic solvent such as tetrahydrofuran, ether, benzene, and the like at from 10°–35°C. for a duration of from 1 to 4 hours. The halides are formed from the alkali metal salt of compound V with the use of an acid halide under moderate conditions such that the cyclicethylene acetal is not destroyed. The reaction is run at from −10° to 10°C. for from 5 minutes to 1 hour. The preferred halide is chlorine and the preferred reagent is oxalyl chloride.

The protected intermediate 2α-carboxy-3α-(1-hydroxyethyl)-1-(6-R$_2$-carbonylhexyl)-5-cyclopentanone, 5-cyclic ethylene acetal, γ-lactone (VI) is reduced by treatment with a moderate reducing agent such as lithium tri-t-butoxy aluminum hydride, lithium borohydride and the like, although the former reducing agent is preferred. The reduction is run in an inert non-reducible solvent such as tetrahydrofuran, ether, ethylene glycol dimethyl ether, and the like. The reaction is generally complete in from 1 to 6 hours at from −80° to 40°C. although the reaction is preferred to be run substantially at from −25° to 25°C. The product is isolated and purified by techniques known to one skilled in this art.

The side-chain aldehyde group of 2α-carboxy-3α-(1-hydroxyethyl)-1-(6-formylhexyl)-5-cyclopentanone, 5-cyclic ethylene acetal, γ-lactone (VII) is protected by forming the cyclic ethylene acetal derivative thereof, viz 2α-carboxy-3α-(1-hydroxyethyl)-1-[6-(1,3-dioxolan-2-yl)hexyl]-5-cyclopentanone 5-cyclic ethylene acetal, γ-lactone (VIII). The procedure is substantially the same as that employed in preparing 2α-carboxy-3α-(1-hydroxyethyl)-5-oxocyclopentaneheptanoic acid 5-cyclic ethylene acetal, γ-lactone, loweralkyl or aralkyl ester (IV) discussed above, and the discussion need not be repeated.

The next step consists of saponification of the lactone to the alkali metal salt of the corresponding hydroxy acid followed by oxidation of the hydroxy group thereof as well as the simultaneous oxidation of the terminal side chain function forming 2α-carboxy-3α-(1,1-dihydroxyethyl)-5-oxocyclopentaneheptanoic acid, carboxymethyl ester (γ-lactone) 5-cyclic ethylene acetal, (IX). The γ-lactone is opened with base catalysis using an alkali metal hydroxide or carbonate such as sodium hydroxide, potassium hydroxide, sodium carbonate and the like. A solvent is generally employed and a loweralkanol is preferred. Sodium hydroxide in methanol is most preferred. The hydrolysis is generally complete in from 1 to 10 hours at from 0°–40°C. The progress of the hydrolysis is followed by taking a thin layer chromatogram of the reaction mixture. When the starting material has disappeared the reaction is complete. The product from the hydrolysis is not isolated but rather the loweralkanol solvent is exchanged for water and the resultant aqueous solution at a pH of from 7–9 treated with an oxidizing agent such as ruthenium tetroxide prepared from ruthenium dioxide and sodium periodate. The progress of the reaction is followed by the formation of the yellow solution of ruthenium tetroxide and, as the oxidation procedes, the reformation of the black precipitate of ruthenium dioxide. The reaction is complete when there is no further production of ruthenium dioxide. Any excess ruthenium tetroxide can be destroyed by the dropwise addition of a loweralkanol or other readily oxidizable substance which, however, must not interfere with or react with the product: 2α-carboxy-3α-(1,1-dihydroxyethyl)-5-oxocyclopentaneheptanoic acid methyl ester (γ-lactone) 5-cyclic ethylene acetal (IX). The product is isolated by techniques known in this art.

The lactone ring of 2α-carboxy-3α-(1,1-dihydroxyethyl)-5-oxocyclopentaneheptanoic acid carboxy methyl ester (γ-lactone)-5-cyclic ethylene acetal is opened by treatment with an alkali metal loweralkoxide or aralkoxide in the presence of the corresponding alkanol, sodium methoxide in methanol being preferred. There results initially the preparation of the 3α-acetyl-2α-carboxylate (IX-A) viz:

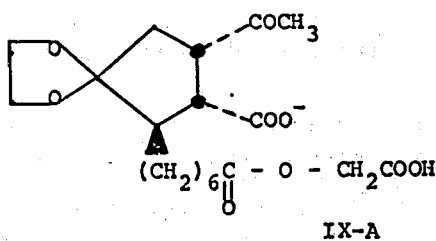

IX-A

The 3α-acetyl group of IX-A is then epimerized and ester interchange of the terminal glycolic acid residue with the alkoxide function present in the reaction mixture takes place, affording 3β-acetyl-2α-carboxy-5-oxo-1β-cyclopentaneheptanoic acid, loweralkyl or aralkyl ester, 5-cyclic ethylene acetal (X). The above steps all occur in situ and the intermediate IX-A is not isolated. The reaction is run substantially at room temperature (15°–35°C.) for from 5 to 25 hours, and the product purified by known techniques.

3β-Acetyl-2α-carboxy-5-oxo-1β-cyclopentaneheptanoic acid, loweralkyl or aralkyl ester 5-cyclic ethylene acetal (X) is oxidized in a Bayer-Villiger reaction using an organic peracid such as trifluoroperacetic acid, m-chloroperbenzoic acid and the like affording 3β-acetoxy-2α-carboxy-5-oxo-1β-cyclopentaneheptanoic acid, loweralkyl or aralkyl ester (XI) 5-cyclic ethylene acetal. The reaction mixture is generally buffered with alkaline buffering agents such as sodium monohydrogenphosphate. The reaction is initially maintained at from −10° to 10°C., and when all of the reagents are combined the temperature of the reaction mixture is raised to from 20°–40°C. for from 1–6 hours. The progress of the reaction is followed with the aid of thin layer chromatography. Additional peracid may be added if the reaction is observed to have stopped before reaching completion.

The carboxylic acid group of 3β-acetoxy-2α-carboxy-5-oxo-1β-cyclopentaneheptanoic acid, loweralkyl or aralkyl ester 5-cyclic ethylene acetal (X) is reduced to the aldehyde group though the imidazolyl, halo, carbazolyl, aziridinyl, or 3,5-dimethylpyrazolyl intermediates (XII) affording 3β-acetoxy-2α-formyl-5-oxo-1β-cyclopentaneheptanoic acid, loweralkyl or aralkyl ester 5-cyclic ethylene acetal, (XIII). The procedure is generally the same as the preparation of the intermediate (VI) and aldehyde (VII) and the discussion need not be repeated.

The aldehyde 3β-acetoxy-2α-formyl-5-oxo-1β-cyclopentaneheptanoic acid, loweralkyl or aralkyl ester 5-cyclic ethylene acetal (XIII) is reacted with dilower-alkyl-2-oxoheptylphosphonate under the conditions of a Wittig reaction to form 3β-acetoxy-5-oxo-2α-(3-oxo-1-octenyl)-1β-cyclopentaneheptanoic acid loweralkyl or aralkyl ester 5-cyclic ethylene acetal, (XIV).

3β-Acetoxy-2α-formyl-5-oxo-1β-cyclopentaneheptanoic acid, loweralkyl or aralkyl ester 5-cyclic ethylene acetal, (XIII) and 3β-loweralkanoyloxy-5-oxo-2α-(3-oxo-1-octenyl)-1β-cyclopentaneheptanoic acid, loweralkyl or aralkyl ester 5-cyclic ethylene acetal, (XIV) are known precursors of prostaglandin $E_1$ and are described in copending U.S. patent application Ser. No. 48,548 filed June 22, 1970 along with the procedures for converting said compounds to $PGE_1$ (XVI).

In order that this invention may be more fully understood the following examples are presented, which examples are given for purposes of illustration and not of limitation.

PREPARATION A

Methyl-8,10-undecadienoate

To a solution of allyl triphenylphosphonium bromide (38.4 g.) in 500 ml. of ether stirred under $N_2$ is added 58 ml. of 1.7 M n-butyl lithium in hexane over 5 minutes. After 20 minutes the stirred mixture is cooled to 0°C. and 17.0 g. of methyl 8-oxo-octanoate in 100 ml. of ether is added over 30 minutes, resulting in discharge of the red ylid color. The mixture is stirred 90 minutes at room temperature, filtered, and the precipitate washed with ether. The combined filtrate and washings are washed with water, saturated aqueous sodium chloride, dried over $MgSO_4$ and concentrated to dryness under vacuum. Distillation of the residue (14.3 g.) at 0.05 mm. gives methyl undeca -8,10 dienoate (7.0 g.) b.p. 65°–70°/0.05 mm. $\lambda_{max}^{CH_3OH}$ 226 mm. (26,700).

EXAMPLE 1

6α-Carboxy-5α-(1-Hydroxyethyl)-2-Cyclohexene-1-Heptanoic Acid Methyl Ester, γ-lactone A solution of methyl 8.10-undecadienoate (8.34 g.) and β-angelicalactone (20.8 g.) is heated in a glass-lined autoclave at 200° for 24 hours. The resulting yellow oil is dissolved in dichloromethane and washed with 5% aqueous sodium bicarbonate, saturated salt solution, dried over $MgSO_4$ and concentrated under vacuum to remove excess β-angelicalactone and cisdiene. The residue (10.92 g.) is chromatographed on 300 g. of silica gel, eluting with 2% acetone in chloroform affording 6.94 g. (70%) of 6α-carboxy-5α-(1-hydroxyethyl)-2-cyclohexene-1-heptanoic acid methyl ester, γ-lactone. $\lambda_{Max}^{CHf}$ 5.68, 5.78 . $\delta_{TMS}^{CDCl_3}$ 1.37 (d, J=7), 2.77 (m, 1H), 3.66 (s, 3H), 4.20 (m, 1H), 5.6–6.0 (m, 2H).

EXAMPLE 2

3-Carboxymethyl-4-Methyl-2-[1-Carboxy-7-(Methoxycarbonyl)Heptyl]-γ-Butyrolactone A stream of 3% ozone in oxygen is passed through a solution of the Diels-Alder adduct: 6α-carboxy-5α-(1-hydroxyethyl)-2-cyclohexene-1-heptanoic acid methyl ester, γ-lactone (5.0 g. 0.0169 moles) in 150 ml. of dichloromethane at about −60°C. until the reaction mixture is saturated with ozone.

The excess ozone is removed in a stream of nitrogen and dichloromethane is removed under reduced pressure to yield the ozonide as a colorless foam after flushing with benzene and ether. The ozonide is dissolved in 150 ml. of acetic acid and 40 ml. of 30% hydrogen peroxide and the mixture is heated at 55°C. under nitrogen for 24 hours. The mixture is evaporated in vacuo at a bath temperature of less than 50°C., flushed with a n-heptane-toluene mixture and the residue extracted into ethyl acetate. The organic extract is washed with cold NaHSO₃ solution, 5% NaHCO₃, salt solution, dried over MgSO₄ and concentrated to give 588 mg. of neutral material. The bicarbonate solution is acidified with saturated NaH₂PO₄ solution and extracted with ethyl acetate. The latter extract is washed with salt solution, dried over MgSO₄ and evaporated to give 3.8 g. (72%) of the crystalline dicarboxylic acid 3-carboxymethyl-4-methyl-2-[1-carboxy-7-(methoxycarbonyl)heptyl]-γ-butyrolactone, m.p. 141°–143° $\lambda_{Max}^{CHf}$ 2.7–3.0, 5.65, 5.75, 5.80μ. $\tau_{MS}^{CDCl_3}$ 1.43 (d, J=7), 3.67 (s, 3H), 4.47 (m, 1H), 10.17 (s, 2H).

EXAMPLE 3

2α-Carboxy-3α-(1-Hydroxyethyl)-5-Oxocyclopentaneheptanoic Acid Methyl Ester, γ-Lactone A solution of 3-carboxymethyl-4-methyl-2-[1-carboxy-7-(methoxycarbonyl)heptyl]-γ-butyrolactone (1.33 g., 3.71 m moles) in 33 ml. of acetic anhydride is refluxed under nitrogen for 1.5 hours. Anhydrous sodium acetate (2.0 g.) is added and the reaction mixture refluxed for an additional 1.5 hours. After cooling to room temperature, sodium acetate is removed by filtration and the mixture is evaporated in vacuo to near dryness after flushing several times with a n-heptane toluene mixture. The last trace of acetic anhydride is removed by cautious addition of a small amount of methanol and again pumping to dryness. The residue is dissolved in dichloromethane and washed with 5% aqueous NaHCO₃, saturated salt solution, dried over MgSO₄ and evaporated to 1.18 g. of a residue consisting of the ketone III and its corresponding enol acetate III-A with the former predominating as evidenced by tlc (5% acetone in chloroform) with (III-A) being more mobile. The conversion of the enol acetate to the ketone is achieved via acid hydrolysis by dissolving the above mixture in 30 ml. of 1.8% methanolic hydrogen chloride. After 16 hours at 25°, the reaction mixture is concentrated in vacuo to provide 1.086 g. of 2α-carboxy-3α-(1-hydroxyethyl)-5-oxocyclopentaneheptanoic acid methyl ester, γ-lactone; $\lambda_{Max}^{CHf}$ 5.66, 5.72, 5.78, $\delta_{TMS}^{CDCl_3}$ 1.43 (d, J=7) 3.66 (s.3 H,) 4.40 (m, 1H).

EXAMPLE 4

2α-Carboxy-3α-(1-Hydroxyethyl)-5-Oxocyclopentaneheptanoic Acid Methyl Ester, γ-Lactone, 5-Cyclic Ethylene Acetal A mixture of 1.184 g. of 2α-carboxy-3α-(1-hydroxyethyl)-5-oxocyclopentaneheptanoic acid methyl ester, γ-lactone, 3.94 ml. of ethylene glycol, 43 mg. of p-toluenesulfonic acid monohydrate in 100 ml. of benzene is azeotropically distilled with a Dean-Stark water separater for 16 hours. The reaction mixture is cooled and quenched into excess aqueous NaHCO₃ solution. The layers are separated and the organic phase is washed with water, saturated salt solution, dried over Na₂SO₄ and evaporated to dryness affording 1.308 g. of 2α-carboxy-3α-(1-hydroxyethyl)-5-oxocyclopentaneheptanoic acid methyl ester, γ-lactone, 5-cyclic ethylene acetal. $\lambda_{Max}^{CHf}$ 5.68, 5.77, 10.52μ; $\delta_{TMS}^{CDCl_3}$ 1.33 (d, J=7), 3.68 (S, 3H), 3.92 (S,4H), 4.42 (m, 1H).

EXAMPLE 5

2α-Carboxy-3α-(1-Hydroxyethyl)-5-Oxocyclopentaneheptanoic Acid 5-Cyclic Ethylene Acetal, γ-Lactone To a stirred solution of 2α-carboxy-3α-(1-hydroxyethyl)-5-oxocyclopentaneheptanoic acid methyl ester, γ-lactone, 5-cyclic ethylene acetal (1.0 g., 2.94 m moles) in 5 ml. methanol is added 5.88 ml. of 1N NaOH. The mixture is stirred at 25°C. for 1.5 hours. Methanol is removed at reduced pressure. The aqueous alkaline solution is poured into saturated aqueous NaH₂PO₄ solution and extracted with ethyl acetate. The latter is extracted with 5% aqueous NaHCO₃. The bicarbonate solution is chilled, acidified with solid NaH₂PO₄ and extracted with ethyl acetate. The organic extract is washed with salt solution, dried over Na₂SO₄ and evaporated to provide 948 mg. (99%) of 2α-carboxy-3α-(1-hydroxyethyl)-5-oxocyclopentaneheptanoic acid 5-cyclic ethylene acetal, γ-lactone. $\lambda_{Max}^{CHf}$ 2.8–3.1, 5.69, 5.78 (sh), 5.83, 10.55μ; nmr $\delta_{TMS}^{CDCl_3}$ 1.38 (d, J=7), 3.93 (s, 4H), 4.45 (m, 1H), 8.40 (s, 1H).

EXAMPLE 6

2α-Carboxy-3α-(1-Hydroxyethyl)-1-(6-Imidazolylcarbonylhexyl)-5-Cyclopentanone, 5-Cyclic Ethylene Acetal, γ-Lactone N,N'-Carbonyldiimidazole (1.24 g., 7.6 m moles) is added to a stirred solution of 2α-carboxy-3α-(1-hydroxyethyl)-5-oxocyclopentaneheptanoic acid 5-cyclic ethylene acetal, γ-lactone (2.36 G., 7.26 m moles) in 25 ml. of dry THF at 25°C. under nitrogen. The reaction mixture is stirred at 25°C. for 2 hours. The solvent is removed in vacuo and the oily residue is dissolved in benzene, washed with water, saturated salt solution, and dried over $Na_2SO_4$ and evaporated to afford 2.60 g. (98.5%) of 2α-carboxy-3α-(1-hydroxyethyl)-1-(6-imidazolylcarbonylhexyl)-5-cyclopentanone, 5-cyclic ethylene acetal, γ-lactone. $\lambda_{Max}^{CHf}$ 3.38, 5.68–5.72, 6.55, 6.79, 7.05, 7.25, 10.55μ. $\delta_{TMs}^{CDCl_3}$ 1.36 (d, J=7), 3.92 (s, 4H), 4.46 (m, 1H), 7.07, 7.48, 8.18 (3H).

EXAMPLE 7

2α-Carboxy-3α-(1-Hydroxyethyl)-1-(6-Formylhexyl)-5-Cyclopentanone, 5-Cyclic Ethylene Acetal, γ-Lactone A solution of lithium tri-t-butoxy aluminum hydride (1.834 g., 7.2 m moles) in 45 ml. dry tetrahydrofuran is added dropwise to a stirred solution of (VI) ($R_2$=imidizalolyl) (2.59 g., 6.87 m moles) in 30 ml. of THF at 25° under nitrogen and the reaction mixture is stirred at 25° for 3 hours. At the end of this period, the solvent is removed under vacuum and to the residue is added benzene and cold saturated aqueous $Na_2SO_4$ solution. Inorganic salts are removed by filtration and the organic phase of the filtrate is washed with water, saturated NaCl solution, dried over $Na_2SO_4$ and evaporated to yield 1.91 g. (90%) of 2α-carboxy-3α-(1-hydroxyethyl)-1-(6-formylhexyl)-5-cyclopentanone, 5-cyclic ethylene acetal, γ-lactone as an oil; $\lambda_{Max}^{CHf}$ 3.70, 5.70, 5.81, 10.55μ; $\delta_{TMs}^{CDCl_3}$ 1.36 (d, J=7), 3.90 (s, 4H), 4.40 (m, 1H), 9.73 (t, 1H).

EXAMPLE 8

2α-Carboxy-3α-(1-Hydroxyethyl)-1-[6-(1,3-Dioxolan-2-yl(hexyl]-5-Cyclopentanone 5-Cyclic Ethylene Acetal, γ-Lactone A mixture of 2α-carboxy-3α-(1-hydroxyethyl)-1-(6-formylhexyl)-5-cyclopentanone, 5-cyclic ethylene acetal, γ-lactone (1.7 g.), p-toluenesulfonic acid monohydrate (250 mg.) in ethylene glycol (25 ml.) and benzene (175 ml.) is azeotropically distilled with a Dean-Stark water separater for 16 hours. The mixture is cooled and added to excess chilled sodium bicarbonate solution. The layers are separated and the aqueous phase is extracted with benzene. The combined organic extracts are washed with water, saturated salt solution dried over $Na_2SO_4$ and concentrated to dryness under vacuum to give 1.91 g. of 2α-carboxy-3α-(1-hydroxyethyl)-1-[6-(1,3-dioxolan-2-yl)hexyl]-5-cyclopentanone 5-cyclic ethylene acetal, γ-lactone as thin needles, m.p. 43°–46°C. $\lambda_{Max}^{CHf}$ 5.68, 10.55μ; $\delta_{TMs}^{CDCl_3}$ 1.33 (d, J=7), 3.92 (m, 8H), 4.52 (m, 1H), 4.87 (t, J=4, 1H).

EXAMPLE 9

2α-Carboxy-3α-(1,1-Dihydroxyethyl)-5-Oxocyclopentaneheptanoic Acid Carboxymethyl Ester, γ-Lactone 5-Cyclic Ethylene Acetal A solution of 2α-carboxy-3α-(1-hydroxyethyl)-1-[6-(1,3-dioxolan-2-yl)hexyl]-5-cyclopentanone 5-cyclic ethylene acetal, γ-lactone (1.0 g., 2.8 m moles), 20% aqueous NaOH (2.0 ml.) in 1.5 ml. of methanol is stirred at 25°C. under a nitrogen atmosphere for 5 hours at which time tlc indicated complete opening of the lactone ring. The mixture is concentrated in vacuo to remove the methanol and 1.5 ml. of water is added. The pH of the solution is adjusted to about 8 with a stream of $CO_2$ gas. Ruthenium dioxide (15 mg.) is then added to the stirred solution followed by dropwise addition of a solution of $NaIO_4$ (2.772 g., 13.0 m moles) in 5–10 ml. of water. The progress of the redox reaction is indicated by the formation of yellow homogeneous ruthenium tetroxide solution followed by reappearance of the black ruthenium dioxide precipitate. When the yellow color persists indicating completion of the reaction, the excess oxidizing agent ($RuO_4$) is destroyed by the addition of a few drops of isopropyl alcohol. The resulting reaction mixture is added to excess cold aqueous $NaH_2PO_4$ solution and extracted with ethyl acetate. The organic phase is washed with water, saturated aqueous NaCl solution, dried over $MgSO_4$ and evaporated to provide 1.067 g. of 2α-carboxy-3α-(1,1-dihydroxyethyl-oxocyclopentaneheptanoic acid carboxymethyl ester, γ-lactone 5-cyclic ethylene acetal; $\lambda_{Max}^{CHf}$ 2.9, 5.69–5.80, 10.55μ; $\delta_{TMs}^{CDCl_3}$ 3.93 (s, 4H), 4.63 (s, 2H), 7.93 (broad S).

EXAMPLE 10

3β-Acetyl-2α-Carboxy-5-Oxo-1β-Cyclopentaneheptanoic Acid Methyl Ester, 5-Cyclic Ethylene Acetal To a solution of 1 g. of 2α-carboxy-3α-(1,1-dihydroxyethyl)-5-oxo-cyclopentaneheptanoic acid carboxymethyl ester, γ-lactone 5-cyclic ethylene acetal in 5 ml. of methanol is added 30 ml. of 0.88N sodium methoxide in methanol under an atmosphere of nitrogen and the reaction mixture is stirred at 25°C. for 16 hours. The reaction mixture is quenched into excess, chilled, saturated $NaH_2PO_4$ and concentrated in vacuo to remove the methanol. The aqueous phase is saturated with salt and extracted with ethyl acetate. The latter extract is washed with salt solution, dried ($MgSO_4$) and evaporated to give 945.4 mg. (96.5%) of 3β-acetyl-2α-carboxy-5-oxo-1β-cyclopentaneheptanoic acid methyl ester, 5-cyclic ethylene acetal; $\lambda_{Max}^{CHf}$ 2.8–3.3, 5.73 sh., 5.80 sh., 5.83, 10.52μ; $\delta_{TMs}^{CDCl_3}$ 2.20 (s, 3H), 3.67 (s, 3H), 3.93 (s, 4H), 9.37 (broad s, 1H).

EXAMPLE 11

3β-Acetoxy-2α-Carboxy-5-Oxo-1β-Cyclopentaneheptanoic Acid Methyl Ester 5-Cyclic Ethylene Acetal Peroxytrifluoroacetic acid is prepared by the dropwise addition of 28 ml. of trifluoroacetic anhydride to 4.4 ml. of 90% $H_2O_2$ in 40 ml. of dichloromethane at 0°C.. The mixture is stirred at 25° for 30 minutes and stored at 0°C. The titer is 1.4 M. Just before use 10 g. of powdered $Na_2HPO_4$ is added portionwise with stirring at 0°C.

To a stirred solution of (883 mg.) of 3β-acetyl-2α-carboxy-5-oxo-1β-cyclopentaneheptanoic acid methyl ester, 5-cyclic ethylene acetal in 17 ml. of dichloromethane at 0°C. is added 10 g. of powdered $Na_2HPO_4$ portionwise. Through a dropping funnel, 24.3 ml. the above $CF_3CO_3H$ solution in $CH_2Cl_2$ is added dropwise during 5 minutes. After the addition is complete, the reaction mixture is allowed to warm to room temperature and stirring is continued for 6 hours. This treatment is then repeated after chilling the reaction mixture to 0°C. and the final reaction mixture is stirred at 25°C. under nitrogen for 16 hours.

After removal of the inorganics by filtration, the filtrate is washed with cold aqueous KI solution followed by cold aqueous $Na_2S_2O_3$) to discharge the iodine color, water, and saturated salt solution. The organic extracts are dried ($MgSO_4$) and evaporated to give 712 mg. of 3β-acetoxy-2α-carboxy-5-oxo-1β- cyclopentaneheptanoic acid methyl ester, 5-cyclic ethylene acetal as an oil. $\lambda_{Max}^{CHf}$ 2.8–33, 5.75 sh., 5.80, 5.83 sh., 10.55$\mu$; $\delta_{TMS}^{CDCl_3}$ 2.05 (s, 3H), 3.67 (s, 3H), 3.97 (s, 4H), 5.24 (m, 1H), 8.37 (broad s, 1H).

EXAMPLE 12

3$\beta$-Acetoxy-2$\alpha$-Imidazolylcarbonyl-5-Oxo-1$\beta$-Cyclopentaneheptanoic Acid Methyl Ester, 5-Cyclic Ethylene Acetal N,N'-Carbonyldiimidazole (164 mg., 1.01 m moles) is added to a stirred solution of 3$\beta$-acetoxy-2$\alpha$-carboxy-5-oxo-1$\beta$-cyclopentaneheptanoic acid methyl ester 5-cyclic ethylene acetal (358 mg., 0.96 m moles) in 4 ml. of dry THF at room temperature under nitrogen. The reaction mixture is stirred at 25°C. under nitrogen for 2 hours. The solvent is removed under vacuum and the oily residue is dissolved in benzene, washed with water, saturated salt solution, dried over Na$_2$SO$_4$ and evaporated to dryness affording 370 mg. of 3$\beta$-acetoxy-2$\alpha$-imidazolylcarbonyl-5-oxo-1$\beta$-cyclopentaneheptanoic acid methyl ester, 5-cyclic ethylene acetal. $\delta_{TMS}^{CDCl_3}$ 2.00 (s, 3H), 3.67 (s, 3H), 4.00 (broad s, 4H), 4.44 (m, 1H), 5.20 (m, 1H), 7.17, 7.37, 8.20 (3H).

EXAMPLE 13

3$\beta$-Acetoxy-2$\alpha$-Formyl-5-Oxo-1$\beta$-Cyclopentaneheptanoic Acid Methyl Ester, 5-Cyclic Ethylene Acetal A solution of lithium tritertiarybutoxy aluminum hydride (120 mg., 0.47 m moles) in 3 ml. dry THF is added dropwise to a stirred solution of 3$\beta$-acetoxy-2$\alpha$-imidazolylcarbonyl-5-oxo-1$\beta$-cyclopentaneheptanoic acid methyl ester, 5-cyclic ethylene acetal (105 mg., 0.235 m moles) in 2 ml. of THF at 25°C. under nitrogen. After 3.5 hours, a thin layer chromatogram (5% acetone in chloroform) of an aliquot indicates the complete absence of the starting amide. The reaction is worked-up after an additional one-half hour by adding it to a chilled mixture of saturated aqueous NaH$_2$PO$_4$ and ethyl acetate, the THF present is removed under vacuum, and the mixture is extracted with ethyl acetate. The organic extract is washed with water, aqueous salt solution, dried over Na$_2$SO$_4$ and concentrated in vacuo to give 75 mg. of 3$\beta$-acetoxy-2$\alpha$-formyl-5-oxo-1$\beta$-cyclopentaneheptanoic acid methyl ester, 5-cyclic ethylene acetal; $\lambda_{Max}^{CHf}$ 3.68, 5.78, 10.52$\mu$; $\delta_{TMS}^{CDCl_3}$ 2.07 (s, 3H), 3.70 (s, 3H), 3.97 (s, 4H), 4.2 (m, 1H), 5.2 (m, 1H), 9.75 (d, J=2, 1H).

EXAMPLE 14

3$\beta$-Acetoxy-2$\alpha$-Formyl-5-Oxo-1$\beta$-Cyclopentaneheptanoic Acid Methyl Ester, 5-Cyclic Ethylene Acetal To a solution of 372 mg. (1 m mole) of 3$\beta$-acetoxy-2$\alpha$-carboxy-5-oxo-1$\beta$-cyclopentaneheptanoic acid methyl ester 5-cyclic ethylene acetal in 5 ml. methanol at 0° is added 2 ml. of 0.5N NaOH dropwise. The mixture is concentrated to dryness under vacuum at 0°C. Benzene (10 ml.) is added and concentrated under vacuum twice to remove traces of water. Benzene (5 ml.) and pyridine (0.1 ml.) are added followed by 1 ml. of oxalyl chloride in 2 ml. of benzene, with the temperature maintained throughout at 0°C. After 15 minutes the mixture is concentrated to dryness, benzene added and the mixture again concentrated to dryness. The residue is dissolved in 5 ml. of diethylene glycol dimethyl ether (diglyme) and cooled to −78°C. To the stirred solution is added dropwise 255 mg. (1 m mole) of lithium-t-butoxy aluminum hydride in 5 ml. of diglyme maintaining the temperature at −78°C. After 20 minutes the mixture is allowed to warm to 20°C., poured onto crushed ice and extracted with ether. The ether extract is washed with water, saturated aqueous sodium chloride, dried over sodium sulfate and concentrated to dryness under vacuum. The residue consists of 3$\beta$-acetoxy-2$\alpha$-formyl-5-oxo-1$\beta$-cyclopentaneheptanoic acid methyl ester, 5-cyclic ethylene acetal with physical properties identical with those of the material obtained from Example 13.

EXAMPLE 15

3$\beta$-Acetoxy-5-Oxo-2$\alpha$-(3-Oxo-1-Octenyl)-1$\beta$-Cyclopentaneheptanoic Acid Methyl Ester, 5-Cyclic Ethylene Acetal A solution of dimethyl 2-oxoheptylphosphonate (138 mg., 0.62 m moles) in 3 ml. of dry THF is added over 3 minutes to a stirred suspension of sodium hydride as a 50% oil dispersion (24.3 mg., 0.507 m moles) in 6 ml. of THF at 0°C. under nitrogen atmosphere. A gelatinous precipitate of the ylid sodium salt forms within 30 minutes. After an additional 30 minutes at 0°C., a solution of 3$\beta$-acetoxy-2$\alpha$-formyl-5-oxo-1$\beta$-cyclopentaneheptanoic acid methyl ester, 5-cyclic ethylene acetal (185 mg., 0.507 m moles) in 5 ml. of THF is added dropwise and the reaction mixture is allowed to warm to room temperature with stirring continued at 25°C. for 3.5 hours. A thin-layer chromatogram (10% acetone in chloroform) indicates the complete disappearance of the starting material. The reaction mixture is cooled to 0°C. and added to chilled saturated NaH$_2$PO$_4$ solution. The mixture is concentrated in vacuo to remove THF and is extracted with ethyl acetate. The latter extract is washed with aqueous sodium chloride, dried over MgSO$_4$ and evaporated in vacuo to provide 285 mg. of residue which is chromatographed on 20 g. of silica gel eluting with 5% acetone in chloroform to provide 161 mg. 3$\beta$-acetoxy-2$\alpha$-formyl-5-oxo-1$\beta$-cyclopentaneheptanoic acid methyl ester, 5-cyclic ethylene acetal which is spectroscopically identical with an authentic sample.

EXAMPLE 16

3-Acetoxy-2-(3-Hydroxy-1-Octenyl)-5-Oxocyclopentaneheptanoic Acid Methyl Ester, 5-Cyclicethylene Acetal To a solution of 40 mg. of 3-acetoxy-2-(3-oxo-1-octenyl)-5-oxocyclopentaneheptanoic acid methyl ester, 5-cyclicethylene acetal in 1.5 ml. of methanol stirred under nitrogen at 0°C. is added 0.4 ml. of a solution of 17 mg. of sodium borohydride in 2 ml. of methanol (3.4 mg. NaBH$_4$). After 30 minutes at 0°C. the mixture is added to 20 ml. of cold saturated aqueous NaH$_2$PO$_4$ and extracted with ethyl acetate. The latter extract is dried over Na$_2$SO$_4$ and concentrated to dryness to give 40 mg. of 3-acetoxy-2-(3-hydroxy-1-octenyl)-5-oxocyclopentaneheptanoic acid methyl ester, 5-cyclicethylene acetal as a mixture of hydroxy epimers on the octenyl side chain. If desired the epimers may be separated at this stage by thin layer chromatography on silica gel (system 10% acetone in chloroform).

EXAMPLE 17

3-Hydroxy-2-(3-Hydroxy-1-Octenyl)-5-Oxocyclopentaneheptanoic Acid, 5-Cyclicethylene Acetal To a stirred solution of 30 mg. of the mixture of epimers of 3-acetoxy-2-(3-hydroxy-1-octenyl)-5-oxocyclopentaneheptanoic acid methyl ester, 5-cyclicethylene acetal obtained in the preceding example in 1 ml. of methanol at 0°C. under nitrogen is added 0.4 ml. of a solution of 88 mg. of potassium hydroxide in 1 ml. of water. The yellow solution is kept at 20°–25°C. for 3 hours. It is then added to cold saturated aqueous $NaH_2PO_4$ (10 ml.) and extracted with ethyl acetate. The latter extract is dried over $Na_2SO_4$ and concentrated to dryness to give 28 mg. of 3-hydroxy-2-(3-hydroxy-1-octenyl)-5-oxocyclopentaneheptanoic acid, 5-cyclicethylene acetal as a mixture of hydroxy epimers on the side chain. The substances are separable on silica gel plates (system-benzene: dioxane: acetic acid: 20:20:1), the most polar component ($R_F$ 0.5) being the desired one.

EXAMPLE 18

3-Hydroxy-2-(3-Hydroxy-1-Octenyl)-5-Oxocyclopentaneheptanoic Acid (+)-Prostaglandin $E_1$)

A solution of 30 mg. of the epimeric mixture of 3-hydroxy-2-(3-hydroxy-1-octenyl)-5-oxocyclopentaneheptanoic acid, 5-cyclicethylene acetal in 2 ml. of 50% aqueous acetic acid is kept at 20°–25°C. for 3 hours. It is then concentrated to dryness to give 28 mg. of crude 3-hydroxy-2-(3-hydroxy-1-octenyl)-5-oxocyclopentaneheptanoic acid, (prostaglandin $E_1$). The product is purified by preparative thin layer chromatography on silica gel (system-benzene: dioxane: acetic acid — 40:40:1) visualizing the components by water spray. The band, which corresponds to prostaglandin $E_1$ is eluted with methanol, the eluate filtered, the filtrate concentrated to dryness and the residue taken up in chloroform. The latter solution is washed with aqueous $NaH_2PO_4$, dried over $Na_2SO_4$ and concentrated to dryness. Crystallization of the residue from ether-hexane gives (±)-prostaglandin $E_1$ m.p. 110°C. The synthetic material has identical tlc mobility as naturally derived prostaglandin $E_1$.

Various changes and modifications may be made in carrying out the present invention without departing from the spirit and scope thereof. Insofar as these changes and modifications are within the purview of the annexed claims, they are to be considered as part of our invention.

What is claimed is:

1. 6α-Carboxy-5α(1-hydroxyethyl)-2-cyclohexene-1-heptanoic acid, γ-lactone, 1–6 carbon loweralkyl, or 6–10 carbon aromatic hydrocarbon substituted lower alkyl ester.

2. The compound of claim 1 in which the ester is the methyl ester.

* * * * *